United States Patent
Gollnick et al.

(10) Patent No.: US 9,050,291 B2
(45) Date of Patent: Jun. 9, 2015

(54) METHODS AND COMPOSITIONS USING PEROXIREDOXIN 1 (PRX1) AS AN ADJUVANT

(75) Inventors: Sandra O. Gollnick, Williamsville, NY (US); Jonah Riddell, Buffalo, NY (US)

(73) Assignee: Health Research Inc., Buffalo, NY (US)

( * ) Notice: Subject to any disclaimer, the term of this patent is extended or adjusted under 35 U.S.C. 154(b) by 731 days.

(21) Appl. No.: 12/963,008

(22) Filed: Dec. 8, 2010

(65) Prior Publication Data

US 2011/0177129 A1  Jul. 21, 2011

Related U.S. Application Data

(60) Provisional application No. 61/267,647, filed on Dec. 8, 2009.

(51) Int. Cl.
| | | |
|---|---|---|
| *A61K 35/00* | (2006.01) | |
| *A61K 39/00* | (2006.01) | |
| *C12N 9/96* | (2006.01) | |
| *A61K 39/39* | (2006.01) | |
| *C12N 9/08* | (2006.01) | |
| *A61K 38/00* | (2006.01) | |

(52) U.S. Cl.
CPC .............. *A61K 35/15* (2013.01); *A61K 39/0011* (2013.01); *A61K 39/39* (2013.01); *A61K 2039/55516* (2013.01); *C12N 9/0065* (2013.01); *A61K 38/00* (2013.01); *C12Y 111/01015* (2013.01)

(58) Field of Classification Search
None
See application file for complete search history.

(56) References Cited

U.S. PATENT DOCUMENTS

| | | | |
|---|---|---|---|
| 6,093,392 A * | 7/2000 | High et al. | 424/93.2 |
| 2003/0124137 A1 | 7/2003 | Dalton et al. | |
| 2007/0172467 A1 | 7/2007 | Itescu | |
| 2009/0048324 A1 | 2/2009 | Jaffe | |
| 2009/0136462 A1 | 5/2009 | Eisenbach et al. | |
| 2009/0246821 A1 | 10/2009 | Lynn et al. | |
| 2009/0291087 A1 | 11/2009 | Scott et al. | |

FOREIGN PATENT DOCUMENTS

| | | | |
|---|---|---|---|
| WO | WO00/60066 | * | 10/2000 |
| WO | 2007089871 A2 | | 8/2007 |
| WO | WO2009/059281 | * | 5/2009 |

OTHER PUBLICATIONS

MESH term definition of Prx1 (downloaded from the Web on Mar. 25, 2013).*
Castelli et al (Cancer Immunol Immunother, 2004, vol. 53, pp. 227-233).*
Lee et al (Journal of Biological Chemistry, 2007, vol. 282, pp. 22011-22022).*
Furuta et al.; Mast cell-mediated immune responses through IgE antibody and Toll-like receptor 4 by malarial peroxiredoxin; Eur. J. Immunol., 2008, vol. 38; pp. 1341-1350.
Auerbach, Robert et al., Angiogenesis Assays: A Critical Overview, Clinical Chemistry, 2003, vol. 49, No. 1, pp. 32-40.
Riddell, Jonah R. et al., Peroxiredoxin 1 Controls Prostate Cancer Growth through Toll-Like Receptor 4-Dependent Regulation of Tumor Vasculature, Cancer Research, Microenvironment and Immunology, Feb. 22, 2011, vol. 71, No. 5, pp. 1637-1646.
Stancovski, Ilana et al., Mechanistic aspects of the opposing effects of monoclonal antibodies to the ERBB2 receptor on tumnor growth, PNAS, Oct. 1, 1991, vol. 88, pp. 8691-8695.
Chen, Miao-Fen et al., Inhibition of Lung Tumor Growth and Augmentation of Radiosensitivity by Decreasing Peroxiredoxin 1 Expression, Int. J. of Raditation Oncology Biol. Phys., 2006, vol. 64, No. 2, pp. 581-591.

\* cited by examiner

*Primary Examiner* — Karen Canella
(74) *Attorney, Agent, or Firm* — Hodgson Russ LLP

(57) ABSTRACT

Provided are compositions and methods for stimulating immune responses against antigens. The compositions contain an antigen to which a stimulated immune response is desired and an isolated Prx1 protein. The Prx1 protein functions as an adjuvant so that the immune response to the antigen stimulated by the composition comprising the antigen and Prx1 is greater than the immune response stimulated by the antigen alone.

5 Claims, 9 Drawing Sheets

METHODS AND COMPOSITIONS USING PEROXIREDOXIN 1 (PRX1) AS AN ADJUVANT

CROSS-REFERENCE TO RELATED APPLICATION

This application claims priority to U.S. application No. 61/267,647, filed Dec. 8, 2009, the disclosure of which is incorporated herein by reference.

FIELD OF THE INVENTION

The present invention is related generally to the field of immunotherapy, and is more specifically related to enhancing an immune response against an antigen by using Prx1 as an adjuvant.

BACKGROUND OF THE INVENTION

Prx1 is a member of the typical 2-cysteine peroxiredoxin family, whose major intracellular functions are as a regulator of hydrogen peroxide signaling through its peroxidase activity and as a protein chaperone. Prx1 expression is elevated in various cancers, including esophageal, pancreatic, lung, follicular thyroid, and oral cancer. Elevated Prx1 levels have been linked with poor clinical outcomes and diminished overall patient survival. Recent studies have demonstrated that Prx1 can be secreted by non-small cell lung cancer cells, possibly via a non-classical secretory pathway. However, until now, the function of secreted Prx1 is unknown and has not been previously exploited for therapeutic purposes.

SUMMARY OF THE INVENTION

The present invention provides compositions and methods for stimulating immune responses. The compositions comprise an antigen and isolated Prx1 protein. The antigen and the Prx1 protein can be provided in a complex, or they may be covalently linked to one another. The Prx1 protein in the complex can be present in a multimer. In one embodiment, the multimer is a decamer. The compositions may further comprise antigen presenting cells that have been exposed to the antigen and/or the Prx1 protein.

The antigen can be any antigen against which a stimulated immune response is desired, including but not necessarily limited to antigens expressed by cancer cells or infectious agents. In one embodiment, the antigen is expressed by tumor cells.

The method for stimulating an immune response to an antigen in an individual comprising administering to the individual a composition comprising the antigen and an isolated Prx1 protein. The stimulated immune response can be greater than the immune response stimulated by the antigen in the absence of administering isolated Prx1 protein. The stimulated immune response can comprise a cell mediated immune response, a humoral immune response and combinations thereof.

In one embodiment, the individual in whom an immune response to an antigen is stimulated is an individual who is a risk for, is suspected of having or has been diagnosed with cancer.

(A) TG-elicited macrophages were analyzed by flow cytometry for expression of CD11b, Gr1, and F4/80. A representative histogram of 3 independent isolations is shown and depicts Gr1 and F4/80 expression by CD11b$^+$ cells. Numbers in the insets indicate the percentages of CD11b$^+$ cells in each quadrant. (B) TG-elicited macrophages were incubated with stimulants for 24 h; supernatants were harvested and analyzed for TNF-α (open bars) and IL-6 levels (gray bars). Results are shown as pg/ml and are representative of three independent experiments; error bars represent standard deviation. (C) TG-elicited macrophages were incubated for 24 h with media only (black bars), 100 nM LPS or 2000 nM Prx1 (open bars), 100 nM LPS or 2000 nM Prx1 pre-incubated for 20 minutes with 10 ug/mL polymyxin B (hatched bars), or 100 nM LPS or denatured 2000 nM Prx1 (gray bars). Asterisks indicate P≤0.01 as compared to cells treated with Prx1 or LPS alone. (D) TG-elicited macrophages were incubated with media alone, Prx1 (50 nM) or LPS (100 nM) for 24 h in the presence (gray bars) or absence (open bars) of 10% FBS. Supernatants were harvested and analyzed for IL-6 levels. Results are shown as pg/ml; error bars represent standard deviation.

Figure 2:
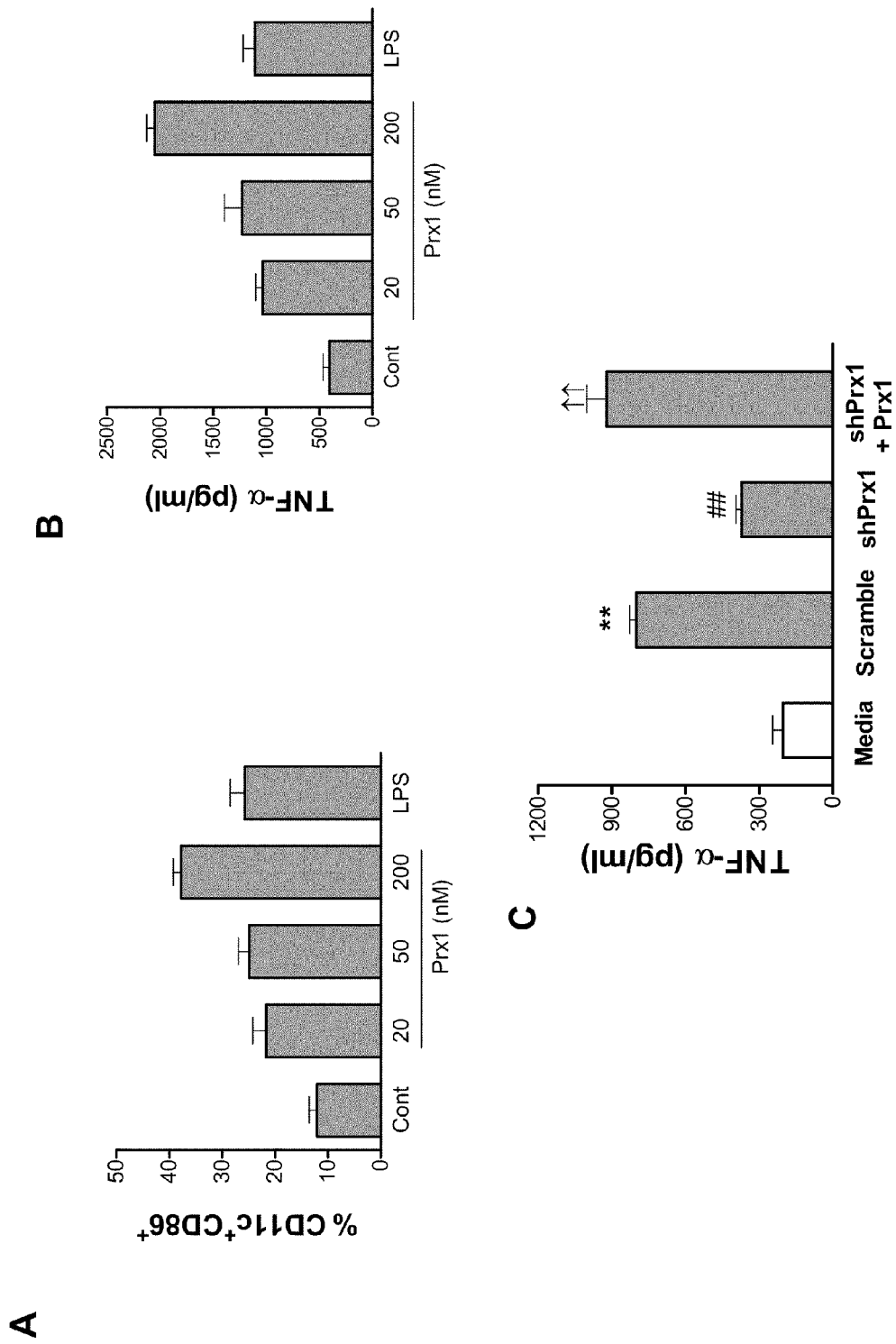

FIG. 2. Prx1 Stimulates Dendritic Cell Maturation and Activation. (A and B)

Immature bone marrow derived dendritic cells (iBMDCs) were incubated with media alone, 20-200 nM Prx1 or 100 nM LPS for 24 h. (A) Following incubation cells were analyzed by flow cytometry for expression of CD11c and CD86. Results are shown as percent total cells; error bars represent standard deviation. (B) Supernatants were harvested and analyzed for TNF-α. Results are shown as pg/ml and are representative of three independent experiments; error bars represent standard deviation. (C) TG-elicited macrophages were incubated with media harvested from prostate tumor cell lines that were transfected with cDNA encoding for either control shRNA (Scramble) or shRNA specific for Prx1 (shPrx1) or in media harvested from cells expressing Prx1 specific shRNA to which 50 nM exogenous Prx1 had been added (shPrx1+ Prx1). Following 24 h incubation, supernatants were harvested and analyzed for TNF-α. Results are shown as pg/ml and are representative of three independent experiments; error bars represent standard deviation. **: P≤0.01 when compared to TNF-α levels secreted by cells incubated with media alone; ##: P≤0.01 when compared to TNF-α levels secreted by cells incubated with media from cells expressing control shRNA; ††: P≤0.01 when compared to TNF-α levels secreted by cells incubated with media from cells expressing shRNA specific for Prx1.

Figure 3:
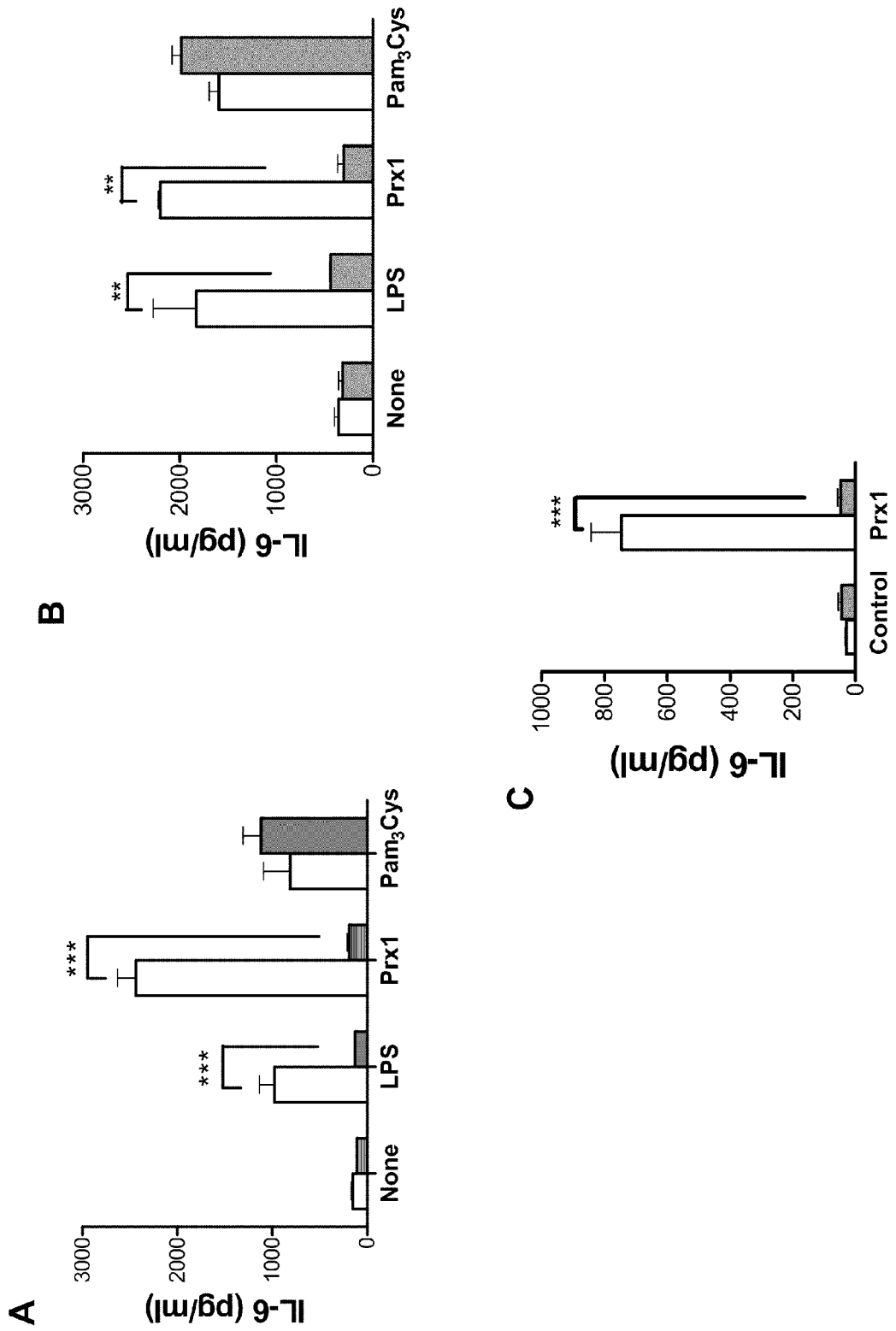

FIG. 3. Prx1 Induced Cytokine Secretion is TLR4 Dependent.

(A) iBMDCs were isolated from C57BL/6 (TLR4$^{+/+}$; open bars) and C57BL/10ScNJ (TLR4$^{-/-}$; closed bars) mice and stimulated with 200 nM Prx1, 100 nM LPS, or 100 mM Pam$_3$Cys. Supernatants were collected and analyzed by IL-6 ELISA kits. (B) TG-elicited macrophages were isolated from C57BL/6 (TLR4$^{+/+}$; open bars) and C57BL/10ScNJ (TLR4$^{-/-}$; closed bars) mice and stimulated with 200 nM Prx1, 100 nM LPS, or 100 mM Pam$_3$Cys. Supernatants were collected and analyzed by IL-6 ELISA kits. Results are presented as pg/ml; error bars represent standard deviation; asterisks indicate P values less that 0.01. (C) Naïve C57BL/6 (TLR4$^{+/+}$; open bars) and C57BL/10ScNJ (TLR4$^{-/-}$; closed bars) mice were injected i.p. with 200 nm Prx1. Six hours later, blood was collected and analyzed by ELISA for the presence of IL-6. Results are presented as pg/ml; error bars represent standard deviation; asterisks indicate P≤0.0002.

Figure 4:
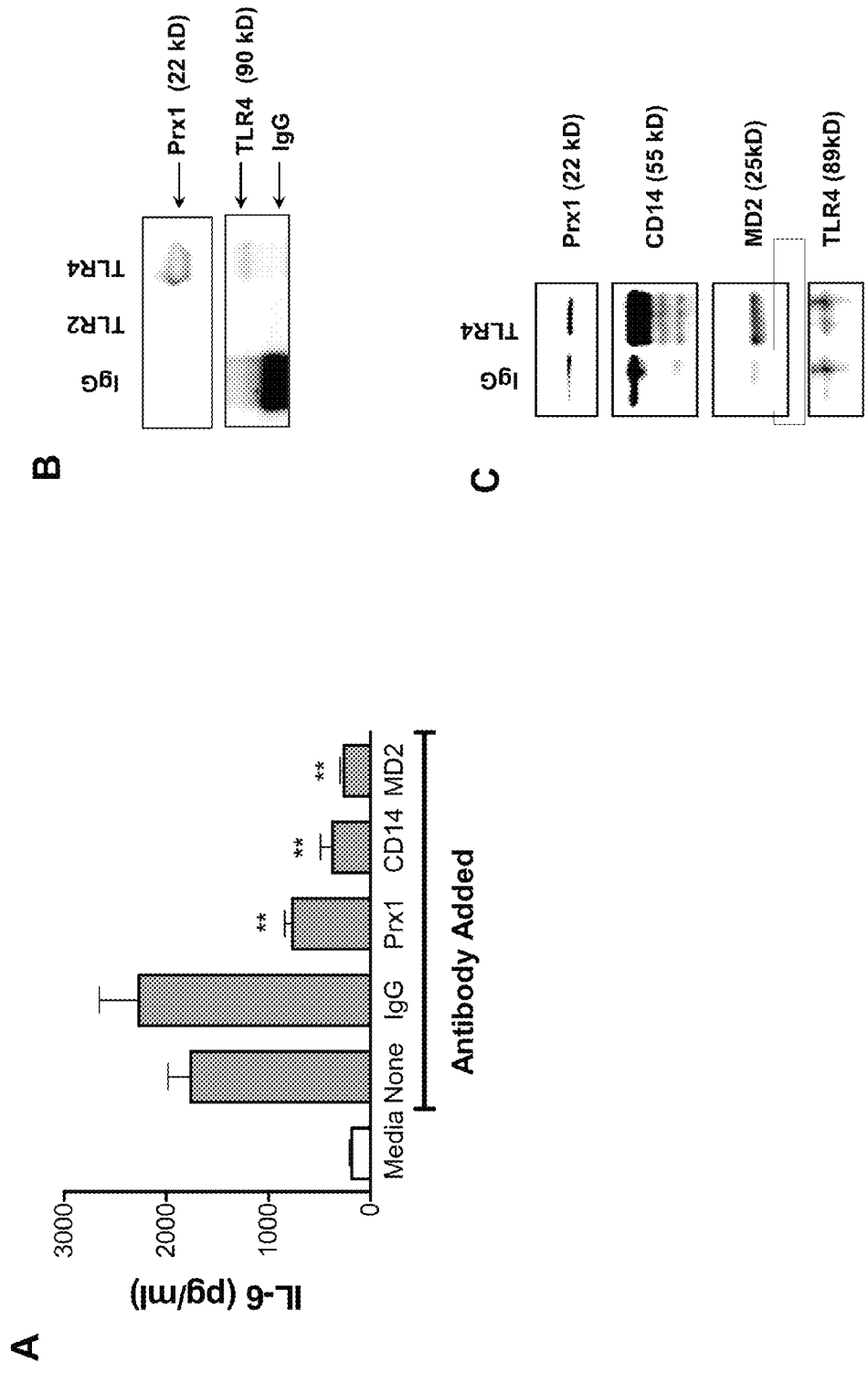

FIG. 4: Interaction of Prx1 with TLR4 is Dependent Upon CD14 and MD2

(A) TG-elicited macrophages were isolated from C57BL/6 mice and stimulated with 50 nM Prx1 in the presence or absence of control or blocking antibodies to Prx1, CD14 or MD2 for 24 h. Supernatants were collected and analyzed by IL-6 ELISA kits. Results are presented as pg/ml; error bars represent SEM; asterisks indicate P values less that 0.01. (B) TG-elicited macrophages were harvested and cell lysates were precipitated with antibodies to TLR4, TLR2, and mouse/goat IgG as described in Materials and Methods; resulting precipitates were separated by SDS-PAGE and probed by Western blot analysis for the presence of Prx1. Blots were also probed with antibodies to TLR4 or TLR2 as a loading control. (C) TG-elicited macrophages were harvested and cell lysates were incubated with antibodies to TLR4 or mouse/goat IgG as described in Materials and Methods; resulting precipitates were separated by SDS-PAGE and probed by Western blot analysis for the presence of Prx1, CD14 and MD2. Blots were also probed with antibodies to TLR4 as a loading control.

Figure 5:
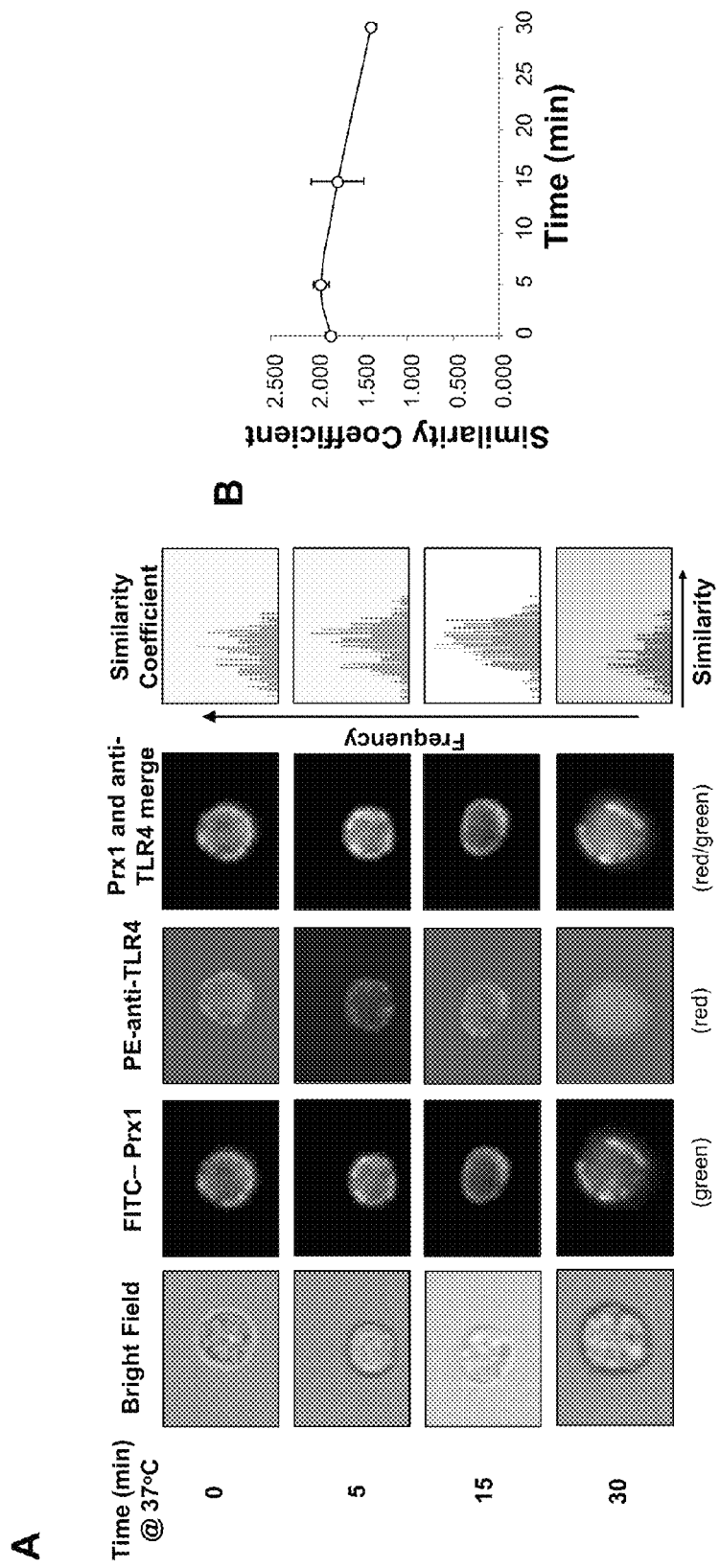

FIG. 5: Kinetics of TLR4/Prx1 Interaction.

(A) TG-elicited macrophages were stimulated with 200 nM FITC-Prx1 or PE-conjugated anti-TLR4 (PE-TLR4). Samples were harvested at the indicated times samples and cell populations were analyzed by Amnis technology. Representative examples of immunostained cells and a merged image of the two stains for each time point are shown. The far right column shows a histogram of the pixel by pixel statistical analysis of each cell (n=5,000) analyzed in which the y-axis is number of cells and the x-axis is the similarity coefficient between Prx1 and TLR4. (B) The average similarity coefficient of all cells for each time point is shown; error bars represent standard deviation.

Figure 6:
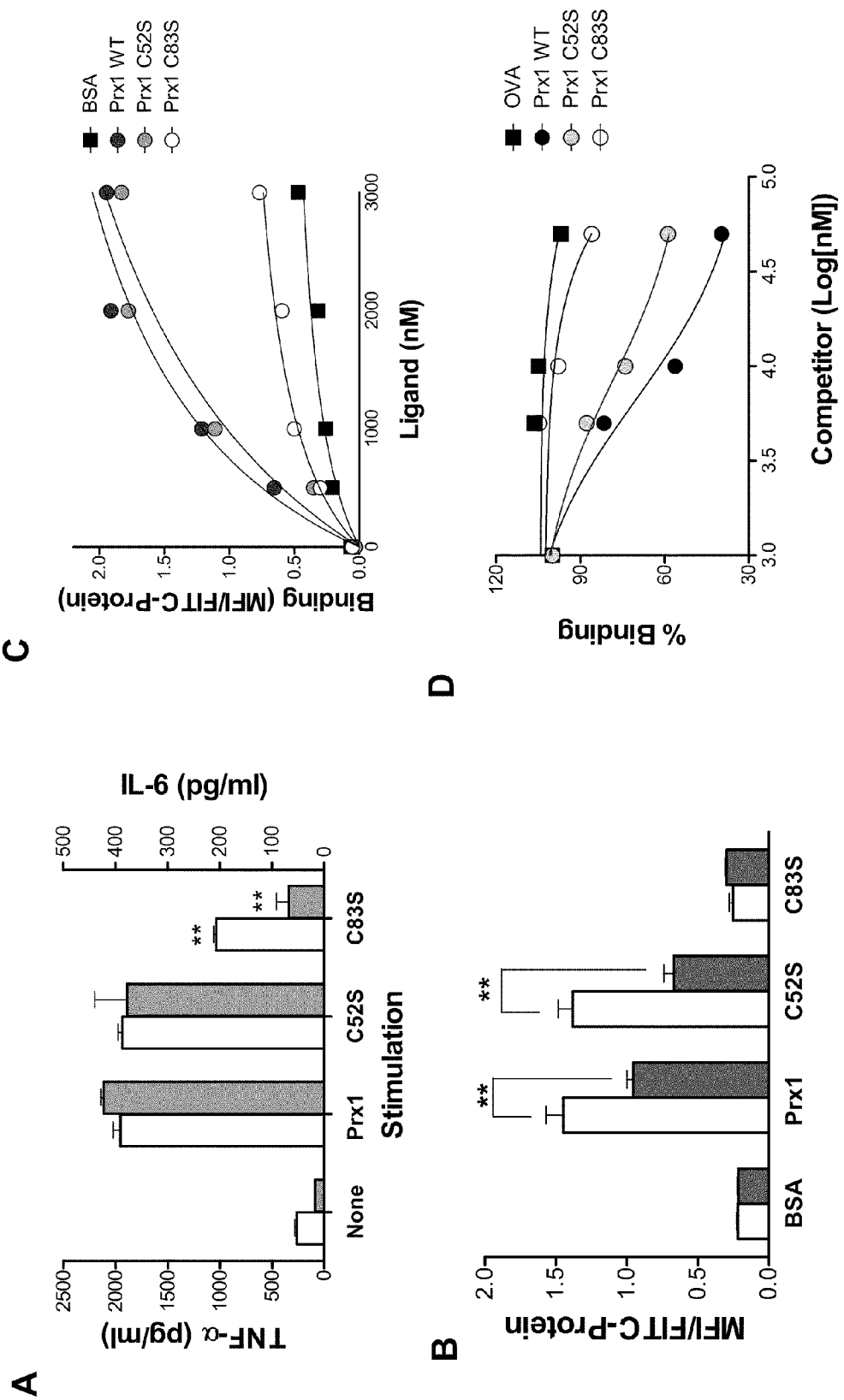

FIG. 6. Prx1 Binding to TLR4 is Structure Dependent (A) TG-elicited macrophages isolated from TLR4$^{+/+}$ (white bars) or TLR4$^{-/-}$ macrophages (filled bars) and incubated with media (None), Prx1, Prx1C52S, or Prx1C83S at 200 nM for 24 h and supernatants were harvested and analyzed for the presence of TNF-$\alpha$ and IL-6. (B) TG-elicited macrophages isolated from TLR4$^{+/+}$ (white bars) or TLR4$^{-/-}$ macrophages (filled bars) and incubated with 2000 nM of FITC-labeled proteins for 20 minutes, followed by analysis by flow cytometry. Viable cells were selected for analysis by elimination of 7-AAD high populations. Results were normalized for any differences in FITC-labeling and reported in MFI/FITC per nM protein; error bars represent standard deviation. Asterisks indicate a P value$\leq$0.01. (C) TG-elicited macrophages were incubated with FITC-BSA (squares), Prx1 (dark circles), Prx1C52S (gray circles), and Prx1C83S (open circles) at various concentrations for 20 min and analyzed by flow cytometry. Results are normalized for differences in FITC-labeling and reported in MFI/FITC per nM protein. Each curve is representative of three individual trials. (D) TG-elicited macrophages were incubated with 1000 nM Prx1, washed and incubated with increasing concentrations of competitors: OVA (squares), Prx1 (dark circles), Prx1C52S (gray circles), Prx1C83S (open circles). Results are shown as a percentage MFI of FITC-Prx1 with no competitor; error bars represent standard deviation. All experiments were performed in triplicate and the combined results are presented.

Figure 7:
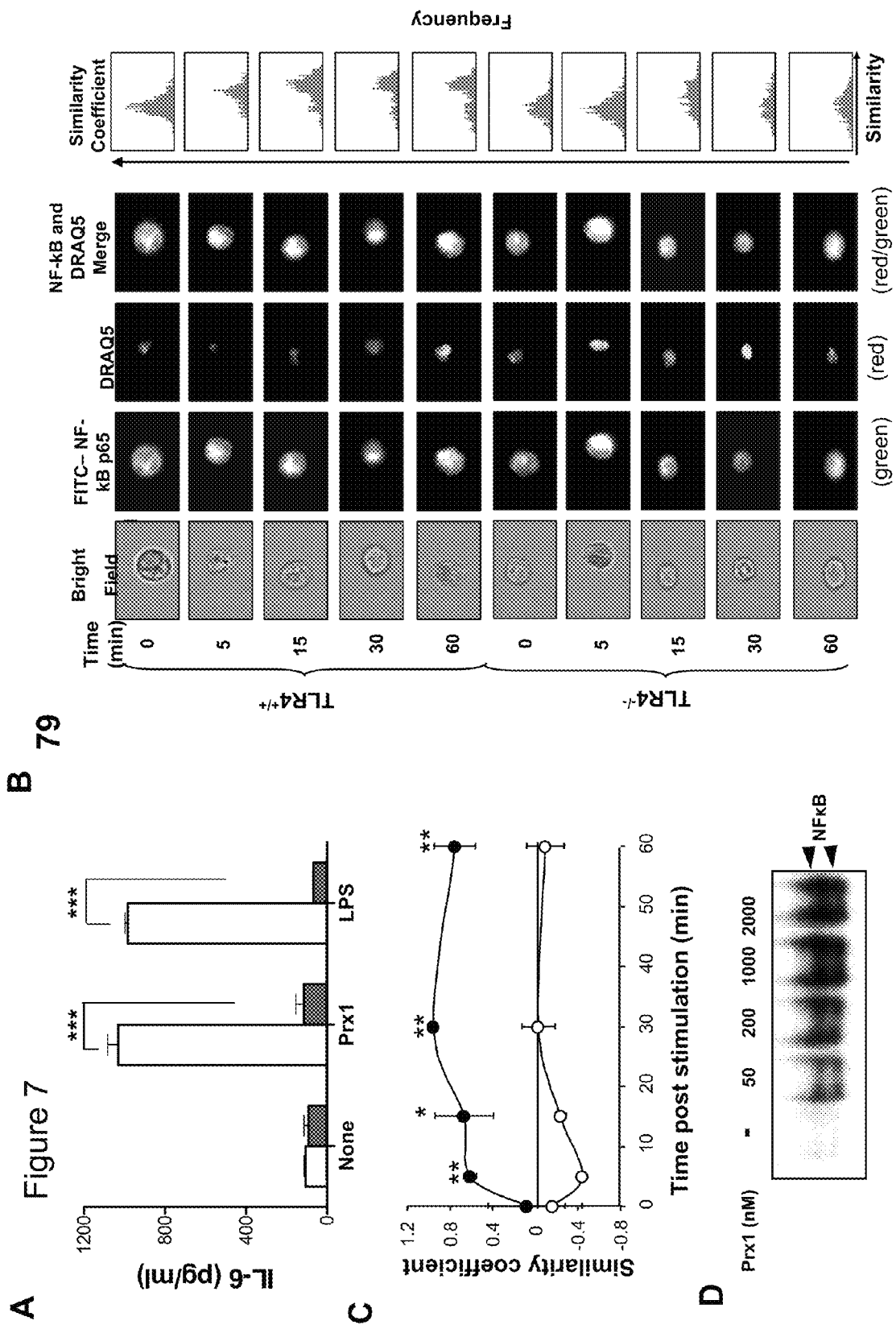

FIG. 7. Prx1 Stimulation of Macrophages is MyD88 Dependent and Leads Nuclear Translocation of NFκB.

(A) Stable transfectants of the RAW264.7 macrophage cell line containing control (open bar) or MyD88 DN (filled bars) expressing plasmids were stimulated with 100 nM LPS or 1000 nM Prx1 for 24 h and the resulting supernatants were assayed for IL-6 expression by ELISA. ELISA analysis was performed in three independent experiments; error bars represent standard deviation. Asterisks indicate a P value$\leq$0.001. (B) TG-elicited macrophages isolated from C3H/HeNCr (TLR4$^{+/+}$) and C3H/HeNJ (TLR4$^{-/-}$) mice were stimulated with 200 nM Prx1 in complete media. At the indicated time points cells were stained with FITC conjugated antibodies to NFκB p65 and DRAQ5 (nuclear stain) for 10 min and analyzed using Amnis technology. The furthest right column shows a pixel by pixel statistical analysis of the similarity of NFκB and nuclear staining (C) The average numerical value of the overall similarity coefficients for each time point in both C3H/HeNCr (filled circles) and C3H/HeNJ (open circles) macrophages is; error bars represent standard deviation. (D) TG-elicited macrophages were incubated with the indicated concentrations of Prx1 for 1 hour. EMSA analysis was performed as described in Example 1.

Figure 8:
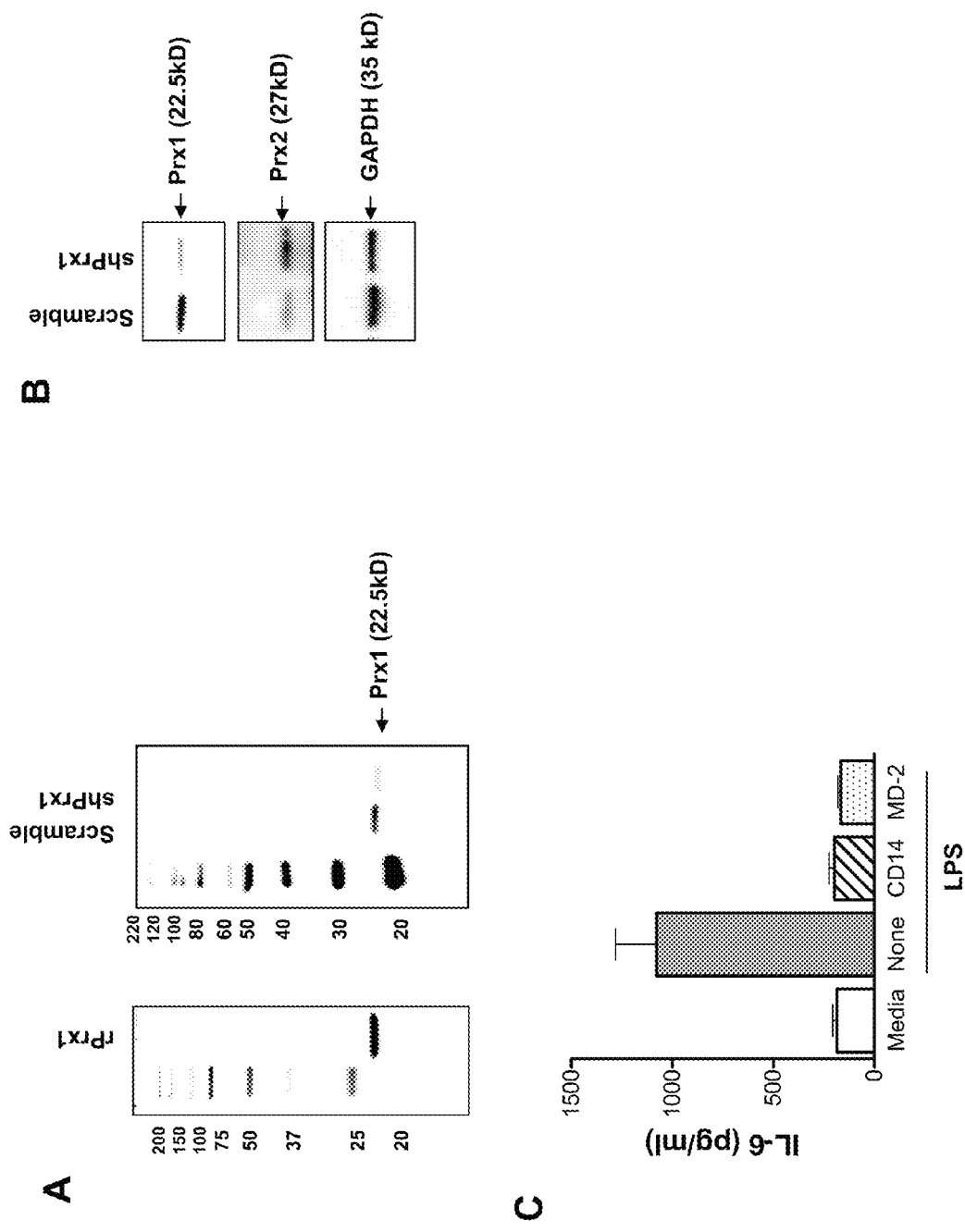

FIG. 8. Expression of shRNA Specific for Prx1 in PC-3M Cells Leads to a Decrease in Prx1 Expression.

(A) Cell lysate isolated from PC-3M cells (right panel) engineered to express control (Scramble) shRNA or Prx1 specific shRNA (shPrx1) was separated by gel electrophoresis, blotted and probed with antibodies specific for Prx1. (B) Expression of shRNA specific for Prx1 leads to decreased Prx1 levels. PC3-M cell lines engineered to express either control shRNA (Scramble) or shRNA specific for Prx1' were harvested and analyzed for expression of Prx1 or Prx2 by Western analysis. (C) Prx1 stimulation of IL-6 secretion from TG-elicited macrophages is dependent upon CD14 and MD2, which are cofactors of TLR4. TG-elicited macrophages were isolated from C57BL/6 mice and stimulated with LPS in the presence or absence of control or blocking antibodies to CD14 or MD2 for 24 h. Supernatants were collected and analyzed by IL-6 ELISA kits. Results are presented as pg/ml; error bars represent SEM.

Figure 9:
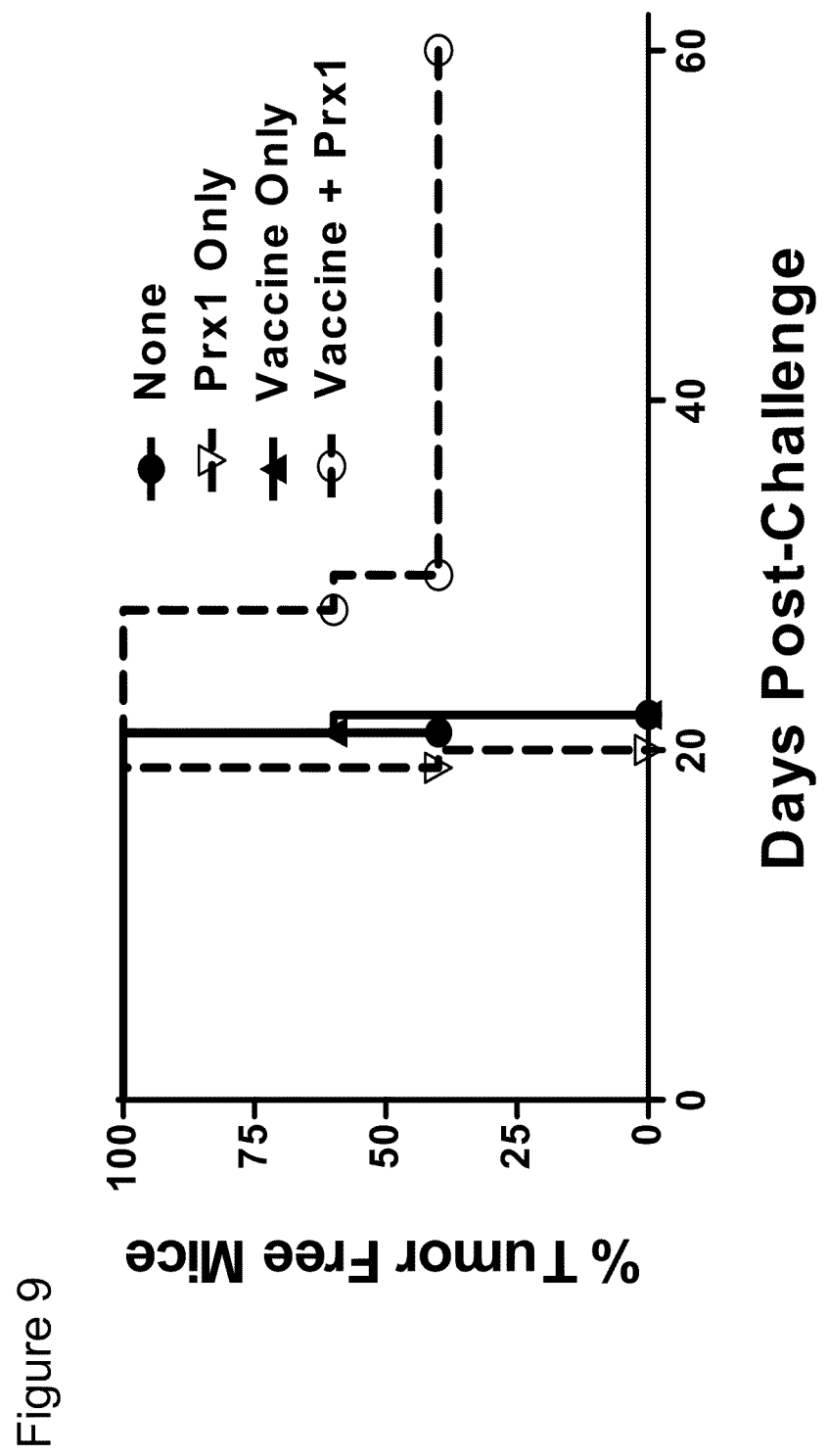

FIG. 9 provides a graphical demonstrating an adjuvant effect of Prx1 against a tumor in an animal model.

DESCRIPTION OF THE INVENTION

The present invention is based on the unexpected discovery that Peroxiredoxin 1 (Prx1) is a ligand for Toll-like receptor 4 (TLR4), and that this function of Prx1 enables it to act as an adjuvant. The invention provides compositions and methods for enhancing an immune response against an antigen in an individual. The composition comprises isolated Prx1 and an antigen. The amino acid sequence of Prx1 and DNA and RNA sequences encoding it are well known in the art. In one embodiment, the isolated Prx1 protein is provided as a decamer. The isolated Prx1 protein can comprise or consist of a 191 amino acid sequence, wherein the protein comprising or consisting of the 191 amino acid sequence has peroxiredoxin activity. In one embodiment, the Prx1 comprises the amino acid sequence shown for NCBI Reference Sequence: NP_859047.1 in the Aug. 23, 2009 entry which is incorporated herein by reference. It is considered that any splice variant and/or Prx1 isomer can be used in the invention.

The method of the invention comprises administering the composition to an individual so that an immune response against the antigen is stimulated. The stimulated immune response can have a therapeutic or prophylactic effect and can include a cell-mediated and/or humoral response, or a combination thereof. The stimulated immune response can be greater than the immune response stimulated by the antigen alone.

Prx1 is an anti-oxidant and chaperone molecule that is found in most cell types and is secreted from transformed and activated cells. TLR4 is a member of the Toll-like receptor (TLR) family. Interaction of TLRs with their ligands initiates the release of inflammatory mediators such as pro-inflammatory cytokines and the maturation/activation of cells of the immune response. Both inflammation and immune cell maturation/activation are required for induction of antigen specific immunity, including anti-tumor immunity. Agents capable of triggering inflammation and immune cell maturation/activation are referred to in the art as adjuvants. We demonstrate herein that Prx1 interacts with TLR4 on the surface of immune cells responsible for induction of antigen specific immunity, such as dendritic cells and macrophages. We also demonstrate that Prx1 interaction with TLR4 leads to production of maturation/activation of dendritic cells and macrophages and secretion of pro-inflammatory cytokines. Thus, it is considered that Prx1 is an immune adjuvant. Importantly, we have demonstrated that addition of Prx1 to an anti-tumor vaccine increase the potency of the vaccine in animals. In this regard, a number of TLR agonists have been used to improve anti-tumor immunity, including the TLR9 agonist CpG motif and the TLR7 agonist Imiquimod. CpG motifs are DNA oligodeoxynucleotide sequences (ODNs) that contain an unmethylated cytosine-guanosine and flanking nucleotides that are capable of binding to TLR9. Imiquimod [1-(2-methylpropyl)-1H-imidazo[4,5-c]quinolin-4 amine; Aldera™; R-837, S26308] is a synthetic TLR7 agonist that can induce the maturation and migration of DCs28, the expression of IFN-α, TNF-α, IL-1α, IL-6, IL-12 and IL-8, and enhance activation of CD8+ T cells. Imiquimod has been used successfully in the treatment of basal cell carcinoma and a recent clinical trial showed that topical imiquimod is effective at clearing stage 0 melanoma. Both of these TLR agonists have been placed on the National Cancer Institute (NCI) priority list for further development as adjuvants for anti-cancer vaccines.

Prx1 exhibits many of the same activities as CpG and imiquimod, however, the receptor to which it binds, TLR4 is more broadly expressed than the TLRs that interact with CpG and imiquimod. Thus, Prx1 has potential to be a more effective anti-cancer vaccine adjuvant.

It is contemplated that the present invention can be used to stimulate an immune response to any antigen, and thus the antigen will function as an immunogen. The antigens include but are not limited to protein, polypeptide or peptide antigens. The antigen may be well characterized, or may be unknown, other than by a known or suspected presence in, for example, a lysate from a particular cell type or any other sample of a biological tissue that contains or could contain the antigen.

In one embodiment, the antigen to which the present invention stimulates an immune response is a tumor antigen. Tumor antigens can be obtained by conventional techniques, such as by preparation of tumor cell lysates by repeatedly freezing and thawing tumor cells/tissues obtained from either fresh tumor biopsy tissues or from tumor cells generated in vitro by tissue culture. The tumor lysate can be obtained by centrifugation and harvesting the supernatant fluid. The tumor cell lysates can be used immediately or frozen and stored until ready for use. The antigen can be used in a purified form or in partially purified or unpurified form as cell lysate. Alternatively, the antigen may be expressed by recombinant DNA techniques in any of a wide variety of expression systems. Thus, it will be recognized that isolated Prx1 proteins may be provided for use in the invention such that discreet, isolated Prx1 proteins are complexed with one antigen, or with different antigens. Such complexes can be formed using various conditions, such as by differing Prx1 to antigen ratios, using a variety of buffers, incubation times, and temperatures.

In one embodiment, the Prx1 protein and the antigen are present in the composition of the invention as a complex, and may be either covalently or non-covalently associated with each other. For example, the Prx1 protein and the antigen may be joined to each other by chemical bonding, such as by covalent bonds, ionic bonds, hydrogen bonds, and/or van der Waals bonds, or combinations thereof. Methods for forming protein/antigen complexes with or without covalent bonding are known in the art and can be employed to form complexes between isolated Prx1 protein and one or more antigens. The complexes of the invention may comprise an isolated Prx1 protein and an antigen, or may consist essentially of a Prx1 protein and an antigen, or may consist of isolated Prx1 protein and an antigen. By "isolated" it is meant that the Prx1 protein is separated from its natural environment. An isolated protein does not necessarily have to be a purified protein. However, isolated Prx1 may nevertheless be purified to any desired degree of purification for use in the present invention. Isolated Prx1 protein includes Prx1 protein produced by recombinant methods. Prx1 multimers, such as decamers, are also considered to be isolated Prx1 proteins according to the invention. Further, isolated Prx1 protein includes Prx1 protein that is linked to an antigen via peptide bonds, such as in a fusion protein. Briefly, to produce such a fusion protein, DNA sequences encoding the Prx1 protein and the antigen can be constructed using conventional techniques and expressed in a suitable cell type using any appropriate expression vector. The fusion protein can then be expressed in the cells and isolated using any method known to those skilled in the art. In one embodiment, the Prx1/antigen fusion protein may be separated by a linker sequence.

Compositions of the invention suitable for administration to an individual can be be prepared by mixing the isolated Prx1 and/or the antigen with any suitable pharmaceutically acceptable carriers, excipients and/or stabilizers. Some examples of compositions suitable for mixing with the agent can be found in: *Remington: The Science and Practice of Pharmacy* (2005) 21st Edition, Philadelphia, Pa. Lippincott Williams & Wilkins.

In one embodiment, the individual in whom an immune response is stimulated according to the method of the invention is an individual who is at risk for, is suspected of having, or has been diagnosed with a cancer. Thus, in various embodiments, the antigen with which the Prx1 protein is an antigen expressed by any type of cancer cell, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia, and heavy chain disease.

In one embodiment, the individual is at risk for, is suspected of having, or has been diagnosed with an infectious agent. Thus, in various embodiments the antigens used in the invention can be those expressed by infections agents. Examples of such infectious agents include, but are not limited to viruses, bacteria, fungi and other parasites. Examples of viruses include, but are not limited to, hepatitis type B or type C, influenza, vaticella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, *M. tuberculosis*, mycobacterium, mycoplasma, *neisseria* and *legionella*. Examples of other parasites include, but are not limited to, *rickettsia* and chlamydia.

The compositions of the invention can be administered using any suitable route of administration. Some non-limiting examples include oral, parenteral, subcutaneous, intraperitoneal, intrapulmonary, and intranasal. Parenteral infusions include intramuscular, intravenous, intraarterial, intraperitoneal, and subcutaneous administration.

Administration of the compositions of the invention can be performed in conjunction with conventional therapies that are intended to treat a disease or disorder associated with the antigen. For example, the composition could be administered prior to, concurrently, or subsequent to conventional anti-cancer therapies. Such therapies can include but are not limited to chemotherapies, surgical interventions, and radiation therapy.

In general, an appropriate dosage and treatment regimen provides the composition in an amount effective to stimulate an immune response that provides a therapeutic and/or prophylactic benefit. Such a response can be monitored by an improved clinical outcome, e.g., inhibition in tumor growth and/or metastasis, improved resistance to infection, improved immune cell activation, and/or other parameters that will be apparent to those skilled in the art, dependant upon the condition being treated.

Routes and frequency of administration of the therapeutic compositions disclosed herein, as well as dosage, will vary from individual to individual, and may be readily established using standard techniques.

In one embodiment, the invention provides a composition comprising an isolated population of antigen presenting cells (APCs) and a complex comprising isolated Prx1 and an antigen. The Prx1/antigen complex can be used to prime APCs, such as dendritic cells, and primed APCs can be administered to an individual to achieve an enhanced immune response against the individual. Thus, the composition comprising an isolated population of APCs and a complex comprising isolated Prx1 and an antigen can be such that all, substantially all, or less than all of the cells in the composition are dendritic cells. Accordingly the cells in the composition can comprise 100% dendritic cells, or between 100% and 10% (including all integers there between) dendritic cells.

In one embodiment, the composition comprising an isolated population of APCs and a complex comprising isolated Prx1 and an antigen is administered to an individual to stimulate a prophylactic or therapeutic immune response in the individual. The APCs administered to the individual may be allogenic or syngeneic.

The following examples are intended to illustrate but not limit the invention.

EXAMPLE 1

This Example provides a description of the materials and methods used in performance of embodiments of the invention.

Materials

Lipopolysaccharide (LPS, *Escherichia coli* serotype 026:B6) polymyxin B sulfate salt, bovine serum albumin (BSA), and ovalbumin (OVA) were obtained from Sigma-Aldrich (St. Louis, Mo.). 7-Amino-Actinomycin D (7-AAD) and thioglycollate brewer modified media was purchased from (Becton Dickinson, La Jolla, Calif.). Capture and detection antibodies for IL-6 and TNF-α used in Luminex assays, as well as protein standards, were purchased from Invitrogen (Carlsbad, Calif.). Antibodies specific for CD11b, Gr-1, F4/80, and all isotypes were purchased from PharMingen (Mountain View, Calif.). Antibodies against TLR2, TLR4, and NFκB subunits were purchased from Santa Cruz Biotechnology (Santa Cruz, Calif.). Blocking antibodies against MD2 and CD14 were purchased from Santa Cruz Biotechnology. The phycoerythrin (PE) conjugated anti-TLR4 antibody was purchased from eBioscience (San Diego, Calif.). Antibodies specific for Prx1 were obtained from Lab Frontier (Seoul, South Korea); this antibody is specific for Prx1 and detects only a single band in Western analysis of cells that express Prx1 (FIG. 8A).

Animals and Cell Lines

C57BL/6NCr (TLR4$^{+/+}$ and TLR2$^{+/+}$), C57BL/10ScNJ (TLR4$^{-/-}$), B6.129-Tlr2$^{tm1Kir/J}$ (TLR2$^{-/-}$), C3H/HeNCr (TLR4$^{+/+}$), and C3H/HeNJ (TLR4$^{-/-}$) pathogen-free mice were purchased from The Jackson Laboratory (Bar Harbor, Me.). Animals were housed in microisolator cages in laminar flow units under ambient light. The mice were maintained in a pathogen-free facility at Roswell Park Cancer Institute (Buffalo, N.Y.). The Institutional Animal Care and Use Committee approved both animal care and experiments.

The role of Prx1 in vivo was determined by injecting either C57BL/6NCr or C57BL/10ScNJ mice intravenously with 90 ug Prx1 (~1000 nM). Cardiac punctures were performed 2 hours later. Serum was obtained by incubation of blood at 4° C. overnight then samples were centrifuged and supernatants collected.

The cultured mouse macrophage cell line (RAW264.7) was maintained in Dulbeco's Modified Eagle Media (DMEM) containing 10% defined fetal bovine serum and 100 U/ml penicillin and 100 ug/ml streptomycin at 37° C. and 5.0% $CO_2$. RAW264.7 cells were transfected with the pcDNA3.1 plasmid containing either control or MyD88 dominant negative (DN) encoding oligonucleotides using FuGENE 6 (Invitrogen, Carlsbad, Calif.) according to the manufacturer's protocol. The transfected cells were then selected using G418 for cells expressing the control or MyD88 DN. Cells were then stimulated with buffer, Prx1, or LPS for 24 h and culture media was harvested for IL-6 cytokine analysis by ELISA.

The retroviral short hairpin RNA expression constructs and retroviral infection procedure used to create a knock down of Prx1 in the lung cancer cell line (A549) is known in the art (Kim, et al; (2007) Cancer Res. 67:546-554, Park, et al. Cancer Res. (2007) 67:9294-9303; Park, et al. 2006. Cancer Res. 66:5121-5129, the disclosures of which are incorporated herein by reference).

Macrophage and Dendritic Cell Isolation

Peritoneal elicited macrophage cells from mice were obtained by an intraperitoneal injection of 1.0 ml of 3.0% (w/v) thioglycollate media (TG). Four days after injection, mice were sacrificed and macrophages were obtained by peritoneal lavage. Macrophages were enriched by adherence selection for 1 h in complete media (DMEM supplemented with 10% defined FBS, 100 U/ml penicillin and 100 μg/ml streptomycin) and were characterized through FACS analysis for expression of CD11b, Gr1 and F4/80 using standard techniques; cells that were CD11b$^+$Gr1$^-$F4/80$^+$ were identified as macrophages.

Immature bone marrow derived dendritic cells were generated by culture of bone marrow derived cells in GM-CSF using standard techniques. Dendritic cells were identified by the expression of CD11c.

Protein Purification

Recombinant human Prx1, Prx1C52S, and Prx1C83S proteins were purified as described previously (Kim, et al. 2006. Cancer Res. 66:7136-7142; Lee, et al. 2007. J. Biol. Chem. 282:22011-22022, the disclosures of each of which are incorporated herein by reference). Briefly, bacterial cell extracts containing recombinant proteins were loaded onto DEAE-sepharose (GE Healthcare, USA) and equilibrated with 20 mM Tris-Cl (pH 7.5). The proteins were dialyzed with 50 mM sodium phosphate buffer (pH 6.5) containing 0.1 M NaCl. The unbound proteins from the DEAE column containing Prx1, Prx1C52S, or Prx1C83S were pooled and loaded onto a Superdex 200 (16/60, GE Healthcare, USA), and equilibrated with 50 mM sodium phosphate buffer (pH 7.0) containing 0.1 M NaCl. The fractions containing Prx1, Prx1C52S, or Prx1C83S were pooled and stored at $-80°$ C. Endotoxin levels of purified proteins were quantified with a *Limulus Amebocyte* Lysate Assay (Lonza, Walkersville, Md.) according to manufacturer's directions. Prx1, Prx1C52S, and Prx1C83S were found to contain $14.14\pm0.050$ EU/ml, $14.07\pm0.67$ EU/ml, and $14.17\pm0.025$ EU/ml respectively.

Cytokine Analysis.

Adherent TG-elicited macrophage cells were washed 5-10 times with PBS, to remove any non-adherent cells. Once washed, complete media containing purified Prx1, Prx1C52S, Prx1C83S, or LPS at the specified concentrations were added in the presence or absence of Prx1, MD-2 and CD14 blocking or control antibodies. In the indicated experiments Prx1 proteins or LPS were incubated with polymyxin B or were boiled for 20 minutes prior to addition. After 24 h the supernatant was collected and analyzed by cytokine specific ELISA or the Luminex multiplex assay system. Serum samples were collected as indicated above and IL-6 levels were determined by ELISA. TNF-α and IL-6 ELISA kits were purchased from BD Bioscience (Franklin Lakes, N.J.) and assays were completed according to manufacturer's instructions.

Luminex analyses were performed by the Institute Flow Cytometry Facility in 96-well microtiter plates (Multiscreen HV plates, Millipore, Billerica, Mass.) with PVDF membranes using a Tecan Genesis liquid handling robot (Research Triangle Park, N.C.) for all dilutions, reagent additions and manipulations of the microtiter plate. Bead sets, coated with capture antibody were diluted in assay diluents, pooled and approximately 1000 beads from each set were added per well. Recombinant protein standards were titrated from 9,000 to 1.4 pg/ml using 3-fold dilutions in diluent. Samples and standards were added to wells containing beads. The plates were incubated at ambient temperature for 120 min on a rocker, and then washed twice with diluent using a vacuum manifold to aspirate. Biotinylated detection antibodies to each cytokine were next added and the plates were incubated 60 min and washed as before. Finally, PE conjugated streptavidin was added to each well and the plates were incubated 30 min and washed. The beads were resuspended in 100 μl wash buffer and analyzed on a Luminex 100 (Luminex Corp., Austin, Tex.). Each sample was measured in duplicate, and blank values were subtracted from all readings. Using BeadView Software (Millipore) a log regression curve was calculated using the bead MFI values versus concentration of recombinant protein standard. Points deviating from the best-fit line, i.e. below detection limits or above saturation, were excluded from the curve. Sample cytokine concentrations were calculated from their bead's mean fluorescent intensities by interpolating the resulting best-fit line. Samples with values above detection limits were diluted and reanalyzed.

FITC Labeling of Proteins

BSA, Prx1, Prx1C52S, and Prx1C83S proteins were conjugated to FITC using a FITC conjugation kit (Sigma, St. Louis, Mo.). A twenty-fold excess of FITC and individual proteins were dissolved into a 0.1M sodium bicarbonate/carbonate buffer (pH adjusted to 9.0); the mix was incubated for 2 h at room temperature with gentle rocking. The excess free FITC was removed with a Sephadex G-25 column (Pharmacia, Piscataway, N.J.). Proteins amounts were quantified using a standard Lowry assay. The F:P (fluorescence:protein) ratio was calculated according to the manufacturer's instructions using the optical density at 495 nm (FITC absorbance) and 280 nm (protein absorbance). FITC per nM protein for BSA, Prx1, Prx1C52S, and Prx1C83S were $31.00\pm1.92$, $38.52\pm2.39$, $74.49\pm2.64$, and $44.44\pm2.64$ respectively.

Saturation Assay

FITC-conjugated BSA, Prx1, Prx1C52S, and Prx1C83S were diluted in 1.0% BSA in PBS to the specified concentrations and a total reaction volume of 100 μL. These mixtures were incubated with $1.0\times10^6$ cells/mL for 20 min on ice to prevent internalization. Cells were washed twice with 1% BSA in PBS and cells were incubated to demonstrate viable from nonviable cells with 7-AAD, less than 30 min before FACsCalibur analysis. Data was acquired from a minimum of 20,000 cells, stored in collateral list mode, and analyzed using the WinList processing program (Verity Software House, Inc., Topsham, Me.). Cells positive for 7-AAD (nonviable) were gated out of the events. FITC-conjugated BSA was used as a negative binding control and for mutant studies variations in FITC labeling were normalized by FITC labeling per nM proteins.

Competition Assay

Unlabeled OVA, Prx1, Prx1C52S, and Prx1C83S were briefly mixed with FITC conjugated Prx1 at the specified concentrations in 100 μL 1.0% BSA in PBS. The mixture was incubated for 20 min on ice, before washing twice with 1.0% BSA in PBS. Cells were then incubated with 7-AAD and analyzed within 30 min by flow cytometry. OVA was used as a negative competition control in all competition assays. Data was acquired from a minimum of 20,000 cells, stored in collateral list mode, and analyzed using the WinList processing program (Verity Software House, Inc., Topsham, Me.). When using WinList to analyze results, 7-AAD positive cells were gated out of the events.

Immunoprecipitation

Immunoprecipitation was carried out with 500 μg of cell lysates and 4 μg of anti-TLR4 or anti-TLR2 overnight at 4° C. After the addition of 25 μL of Protein G-agarose (Santa Cruz Biotechnology), the lysates were incubated for an additional 4 h. To validate specific protein interactions, goat IgG (Santa Cruz Biotechnology) or mouse IgG (Santa Cruz Biotechnology) was used as negative control. The beads were washed thrice with the lysis buffer, separated by SDS-PAGE, and immunoblotted with antibodies specific for Prx1. The proteins were detected with the ECL system (Biorad).

Co-Localization of Prx1/TLR4 and NFκB Translocation

Colocalization experiments were performed by the addition of 200 nM FITC-labeled Prx1 and PE-conjugated anti-TLR4 to the media of TG-elicited macrophages and kept at 37° C. for the indicated times before being transferred to ice, fixed and analyzed. Immunostaining to detect the nuclear translocation of NFκB was performed in the following manner. TG-elicited macrophages obtained from C3H/HeNCr (TLR4$^{+/+}$) and C3H/HeNJ (TLR4$^{-/-}$) were treated with 200 nM Prx1. After the indicated times at 37° C. the cells were then scraped and collected in tubes, washed twice in wash buffer (2% FBS in phosphate-buffered saline), and then fixed in fixation buffer (4% paraformaldehyde in phosphate-buffered saline) for 10 min at room temperature. After washing, the cells were re-suspended in Perm Wash buffer (0.1% Triton X-100, 3% FBS, 0.1% sodium azide in phosphate-buffered saline) containing 10 µg/ml anti-NF B p65 antibody (Santa Cruz Biotechnology) for 20 min at room temperature. The cells were then washed with Perm Wash buffer and resuspended in Perm Wash buffer containing 7.5 µg/ml FITC conjugated F(ab')$_2$ donkey anti-rabbit IgG for 15 min at room temperature. Cells were washed twice in Perm Wash buffer and re-suspended in 1% paraformaldehyde containing 5 µM DRAQ5 nuclear stain (BioStatus) for 5 min at room temperature.

Image Analysis

Co-localization of Prx1 and TLR4 and nuclear translocation of NFκB were analyzed with the ImageStream® multispectral imaging flow cytometer (Amnis Corp., Seattle, Wash.). At least 5000 events were thus acquired for each experimental condition and the corresponding images were analyzed using the IDEAS® software package. A hierarchical gating strategy was employed using image-based features of object contrast (gradient RMS) and area versus aspect ratio to select for in-focus, single cells. Co-localization and nuclear translocation was determined in each individual cell using the IDEAS® similarity feature which is a log transformed Pearson's correlation coefficient of the intensities of the spatially correlated pixels within the whole cell, of the Prx1 and TLR4 images or NFκB and DRAQ5 images, respectively. The similarity score is a measure of the degree to which two images are linearly correlated.

Electrophoretic Mobility Shift Assay (EMSA)

EMSA was performed using conventional techniques. Briefly, 10 µg of nuclear protein was incubated with γ-$^{32}$P-labeled double-stranded NFκB oligonucleotide in 20 µL of binding solution containing 10 mM HEPES (pH 7.9), 80 mM NaCl, 10% glycerol, 1 mM DTT, 1 mM EDTA, 100 µg/mL poly(deoxyinosinic-deoxycytidylic acid). The DNA-protein complexes were resolved on a 6% polyacrylamide gel under non-denaturing conditions at 200 V for 2 h at 4° C. Gels were dried and then subjected to autoradiography.

Statistical Analysis

Statistical analyses were performed using a standardized t-test with Welch's correction, where equal variances were not assumed, to compare experimental groups. Differences were considered significant when P values were ≤0.05.

EXAMPLE 2

This Example provides a description of results obtained using the materials and methods described in Example 1.

Prx1 Stimulation of Cytokine Secretion from DCs and TG-Macrophages and Maturation of DCs is Dependent Upon TLR4

Thioglycolate (TG)-elicited murine macrophages were used to assess the ability of Prx1 to stimulate cytokine secretion. Macrophage phenotype was assessed by analysis of peritoneal exudate cell populations for CD11b, Gr1, and F4/80 expression. The isolated populations were greater than 99% CD11b$^+$ and of the CD11b$^+$ cell population a majority were Gr1$^-$, F4/80$^+$ (FIG. 1A). Stimulation of TG-elicited macrophages with Prx1 resulted in the dose dependent secretion of TNF-α and IL-6 that was significantly greater than that observed in unstimulated cells at all doses (P≤0.01; FIG. 1B). Pre-incubation of Prx1 with the endotoxin inactivator polymixin B had no significant effect on Prx1 stimulation of cytokine secretion (FIG. 1C); in contrast, denaturing of Prx1 significantly reduced its ability to stimulate cytokine secretion (P<0.01).

Stimulation of cytokine secretion by TG-elicited macrophages following incubation with Prx1 was significantly diminished in the absence of serum (P≤0.01; FIG. 1D); however even in serum free conditions, incubation of TG-elicited macrophages with Prx1 significantly increased IL-6 secretion (P≤0.005 when compared to secretion by cells incubated in serum free media). Prx1 was also able to stimulate cytokine secretion from the cultured dendritic cell line, DC1.2, and the murine macrophage cell line, RAW264.7 (data not shown).

Exogenous Prx1 was able to induce maturation and activation of immature bone marrow derived DCs (iBMDCs). iBMDCs were incubated with increasing concentrations of Prx1 for 24 h and examined for cell surface expression of co-stimulatory molecules and secretion of TNF-α. Addition of Prx1 led to significant dose dependent increase in cell surface expression of the co-stimulatory molecule, CD86 (FIG. 2A) and TNF-a secretion (FIG. 2B) at all doses tested (P≤0.01 when compared to control).

It is possible that enhanced secretion of cytokines from iBMDCs and TG-elicited macrophages upon addition of exogenous recombinant Prx1 is a phenomena of the recombinant protein and not physiologically relevant. To begin to determine whether Prx1 could promote cytokine secretion in a physiologic context, TG-elicited macrophages were incubated for 24 h in the presence of supernatant collected from Prx1-secreting tumor cells or supernatant collected from tumor cells engineered to express shRNA specific for Prx1. Expression of shRNA resulted in reduced expression of Prx1, but not Prx2 FIG. 8B). Incubation of TG-elicited macrophages with supernatants of tumor cells engineered to express a non-specific shRNA, resulted in enhanced expression of TNF-α (Sc, FIG. 2C; P≤0.0001 when compared to media). In contrast, TG-elicited macrophages incubated with supernatants collected from tumor cells expressing reduced levels of Prx1 secreted significantly lower levels of TNF-α (P≤0.0001 when compared to incubation with supernatant harvested from cells expressing control shRNA; FIG. 2C); addition of exogenous Prx1 to these supernatants restored TNF-α secretion from TG-elicited macrophages (shPrx1+Prx1; P≤0.003 when compared to incubation with supernatant harvested from cells expressing shRNA specific for Prx1).

To test whether Prx1 activation of iBMDCs and TG-elicited macrophages was dependent upon TLR4, iBMDCs and TG-elicited macrophages were isolated from C57BL/6NCr (TLR4$^{+/+}$) and C57BL/10ScNJ (TLR4$^{-/-}$) mice and stimulated with Prx1, LPS or Pam$_3$Cys, a TLR2 agonist. The results indicate that Prx1, LPS, and Pam$_3$Cys stimulate cytokine secretion from iBMDCs (FIG. 3A) and macrophages isolated from C57BL/6NCr mice (FIG. 3B); only Pam$_3$Cys stimulated cytokine secretion from iBMDCs and macrophages isolated from C57BL/10ScNJ mice (P≤0.01 when compared to cytokine secretion by cells isolated form C57BL/NCr mice).

The ability of Prx1 to induce TLR4 dependent inflammation in vivo was tested by i.p. injection of recombinant Prx1 into either C57BL/6NCr (TLR4$^{+/+}$) or C57BL/10ScNJ (TLR4$^{-/-}$) mice. Blood was collected 2 h post injection and the extent of systemic inflammation was determined by assessing the level of systemic IL-6 (FIG. 3C). Injection of Prx1 resulted in a significant increase in systemic IL-6 levels (P≤0.0002) in C57BL/6NCr (TLR4$^{+/+}$) mice, but had no significant effect on systemic IL-6 levels in C57BL/10ScNJ (TLR4$^{-/-}$) mice.

The reduced expression of cytokines by TG-elicited macrophages following incubation with Prx1 in the absence of serum (FIG. 1D) suggests that serum proteins may contribute to optimal Prx1/TLR4 interaction. Many TLR4 ligands interact with TLR4 as part of a larger complex that can include CD14 and/or MD2. To determine whether Prx1 enhancement of cytokine secretion from TG-elicited macrophages involves CD14 or MD2, cells were incubated with Prx1 or LPS in the presence of blocking antibodies to MD2, CD14 or control IgG (FIG. 4A). Addition of blocking antibodies to Prx1, CD14 or MD2 significantly inhibited the ability of Prx1 to stimulate IL-6 secretion from TG-elicited macrophages when compared to that induced by Prx1 in the presence of control IgG ($P \leq 0.01$). Blocking antibodies to CD14 and MD2 also blocked cytokine secretion in LPS stimulated cells (FIG. 8C).

To further demonstrate the interaction Prx1 and TLR4/MD2/CD14, TG-elicited macrophage cell lysates were incubated with isotype control antibodies or antibodies specific for TLR4 or TLR2 (FIG. 4B). The antibody complexes were isolated and immunoblotting was performed using antibodies to Prx1; Prx1 was only found in the lysates immunoprecipitated with TLR4 (FIG. 4B). The TLR4/Prx1 complexes isolated from Prx1 treated cells also contained CD14 and MD2 (FIG. 4C), confirming the finding that Prx1 interacts with TLR4 in a complex that contains both CD14 and MD2.

The kinetics of the Prx1 and TLR4 interaction was determined using image stream analysis (Amnis) to examine co-localization of the two molecules. TG-elicited macrophages were incubated with FITC-labeled Prx1 and PE-conjugated anti-TLR4 antibodies. The merged images of representative cells indicate that Prx1 and TLR4 localize together on the membrane of the macrophage within 5 minutes and that by 30 min, TLR4 and a portion of the Prx1 molecules have been internalized (FIG. 5A). The histograms to the right of the merged images are a statistical analysis of the similarity of FITC-Prx1 and PE-anti-TLR4 in 5,000 cells on a pixel-by-pixel basis. A shift of this distribution to the right indicates a greater degree of similarity. The average similarity coefficient at each time point was demonstrated in FIG. 5B. At all time points there was a high similarity of Prx1 and TLR4 staining (similarity coefficients>1), indicating a co-localization Prx1 and TLR4. These results confirm that Prx1 and TLR4 interact on the cell surface and that at least of portion of the Prx1 is internalized with TLR4.

Stimulation of Cytokine Secretion and Binding to TLR4 Depends Upon Prx1 Structure Prx1 acts as both a peroxidase and a protein chaperone (Wood, et al. (2003) Trends Biochem. Sci. 28:32-40). To determine whether the ability of Prx1 to stimulate cytokine secretion from TG-elicited macrophages was related to its peroxidase activity and/or chaperone activity, two Prx1 mutants were examined. The Prx1C52S mutant lacks peroxidase activity but retains the decamer structure needed for chaperone activity; Prx1C83S exists mainly as a dimer, has reduced chaperone activity and intact peroxidase activity. Cytokine secretion following Prx1C52S stimulation of TG-elicited macrophages was not significantly distinct from that observed following stimulation with Prx1 (FIG. 6A); however, TG-elicited macrophages stimulated with Prx1C83S displayed a significant reduction in cytokine secretion ($P \leq 0.01$).

Prx1 binding to TG-elicited macrophages was dependent upon the presence of TLR4 as binding of Prx1 and the enzymatic null mutant (Prx1C52S) was significantly decreased in the absence of TLR4 (FIG. 6B). Prx1C83S binding was minimal to either TLR4 expressing or non-expressing macrophages, confirming that Prx1 interaction with TLR4 is peroxidase independent and structure dependent.

Saturation binding (FIG. 6C) and competition analyses (FIG. 6D) were used to determine the $K_d$, and $K_i$ values for Prx1 binding to the surface of TG-elicited macrophages. The $K_d$ for Prx1 binding to TG-elicited macrophages was 1.6 mM and the $K_i$ was 4.1 mM (Table 1).

Prx1 Stimulation of Cytokine Secretion is MyD88-Dependent and Leads to TLR4-Dependent Translocation of NFκB to the Nucleus The consequential downstream signaling events of ligand-mediated activation of TLR4 can be MyD88 dependent or independent. Prx1 was used to stimulate cytokine expression from RAW264.7 cells expressing dominant negative (DN) MyD88 protein. IL-6 secretion following Prx1 stimulation is dependent on MyD88 function (FIG. 7A), indicating that Prx1 activates the MyD88 signaling cascade, which can lead to activation of NFκB.

To determine if Prx1/TLR4 interaction leads to NFκB activation, NFκB translocation following Prx1 stimulation was analyzed in macrophages isolated from C3H/HeNCr and C3H/HeNJ mice. C3H/HeNJ mice have a mutation in the TLR4 ligand binding domain that prevents ligand binding. TG-elicited macrophages from C3H/HeNCr and C3H/HeNJ mice were incubated with 200 nM Prx1 at 37° C. for the indicated times, transferred to ice and incubated with antibodies against NFκB p65; the nuclear stain DRAQ5 was added 15 minutes prior to image stream analysis. Prx1 incubation with macrophages isolated from C3H/HeNCr mice triggered NFκB translocation within 5 min and nuclear localization was apparent for up to 60 min (FIG. 7B). In contrast Prx1 incubation with macrophages isolated from C3H/HeNJ mice did not trigger NFκB translocation (FIG. 7B). The histogram to the right of the merged image column depicts the similarity of NFκB and the nuclear stain on a pixel-by-pixel basis. Prx1 stimulation led to NFκB translocation to the nucleus in a TLR4 dependent manner as demonstrated by the positive similarity coefficient observed following Prx1 stimulation of C3H/H3NCr TG-elicited macrophages, which was decreased following Prx1 stimulation of C3H/HeNJ TG-elicited macrophages (FIG. 7C). The ability of Prx1 to activate NF-κB was confirmed by EMSA, which indicated that incubation of macrophages with Prx1 resulted in a dose dependent increase in NFκB DNA binding activity (FIG. 7D).

It will be recognized by those skilled in the art that the foregoing results are compelling evidence that Prx1 stimulates TLR4-dependent secretion of TNF-α and IL-6 from TG-elicited macrophages and DCs. Cytokine secretion was the result of TLR4 stimulation of the MyD88-dependent signaling cascade and resulted in activation and translocation of NFκB. Prx1 is an intercellular protein that is secreted from tumor cells and activated T cells. The ability of Prx1 to interact with TLR4 and stimulate the release of pro-inflammatory cytokines suggests that it may also act as an endogenous damage-associated molecular pattern molecule (DAMP).

HSP72 and HMGB1, which have also been classified as endogenous DAMPs, have been shown to interact with TLR4. Saturation and competition studies indicate that Prx1 has a $K_d$ of ~1.3 mM and a $K_i$ of ~4.1 mM; extrapolation of data presented by Binder et al. (Binder, et al. 2000. J. Immunol. 165:2582-2587) implies that HSP72 has a $K_d$ of 2.1-4.4 mM and a $K_i$ of 10-21.8 mM, suggesting that Prx1 interaction with TLR4 is stronger than that of HSP72. Binding affinities are not available for HMGB1.

Figure 1:
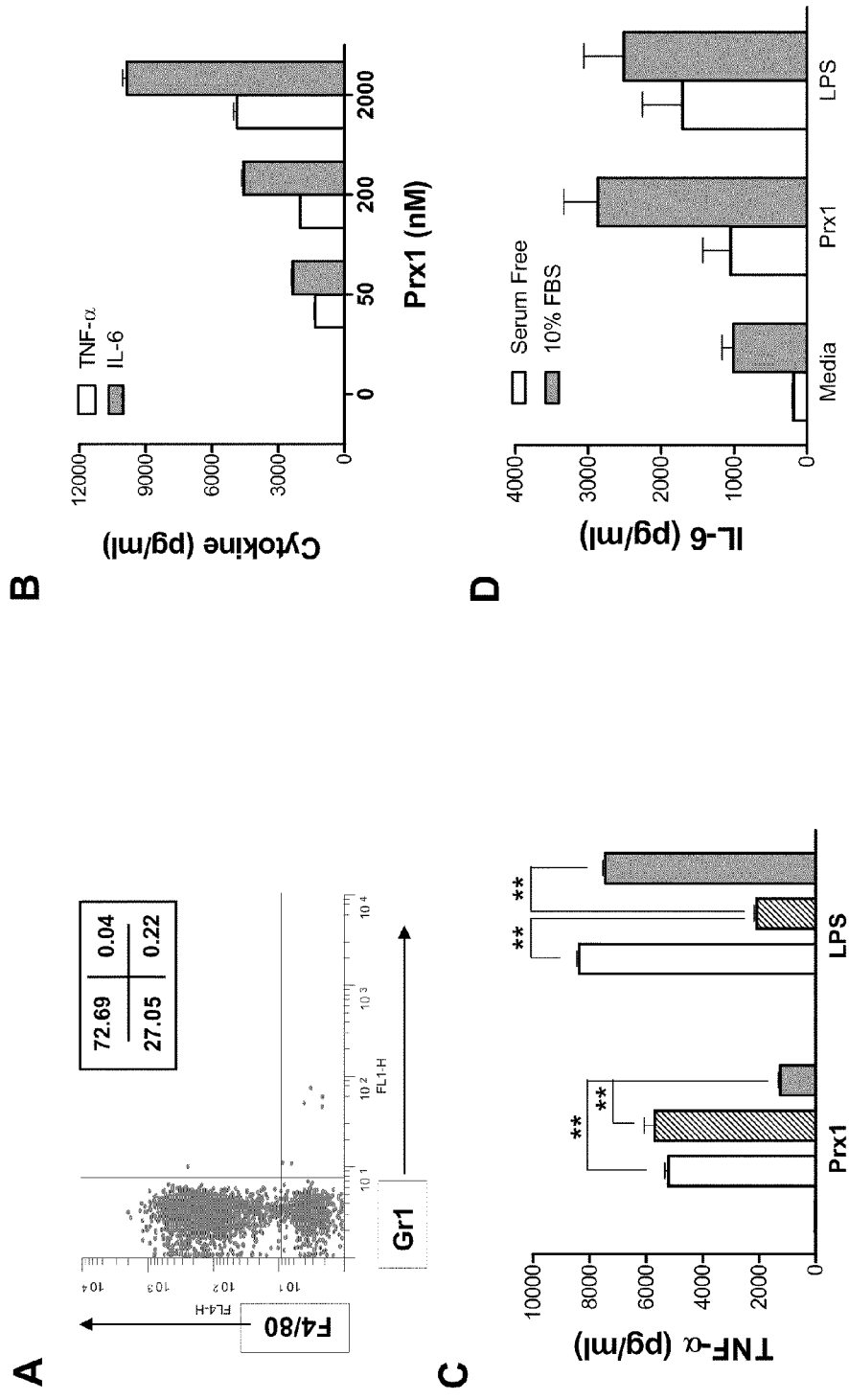
FIG. 1. Prx1 Stimulates Cytokine Secretion from Macrophages.

Identification of TLR4 as a receptor for a recombinant protein may be complicated by the potential of the presence of LPS within a recombinant protein preparation. To account for this possibility in the results presented here, two controls were included in all of the performed studies. In the first control, recombinant proteins were combined with polymixin B prior to their addition to immune cells. Polymixin B is a powerful inactivator of LPS; pre-incubation of recombinant Prx1 with polymixin B had no effect on the ability of Prx1 to stimulate cytokine expression (FIG. 1). However pre-incubation of LPS with the same concentration of polymixin B significantly inhibited its ability to stimulate cytokine release. As a second control, Prx1 and LPS were boiled prior to addition to immune cells; denaturing Prx1 significantly inhibited its ability to stimulate cytokine release, but boiling had no effect on the ability of LPS to stimulate cytokine release. Finally, all of the recombinant proteins used in this study were prepared in the same fashion and following purification all were found to have equivalent levels of endotoxin (~14 EU/ml), yet Prx1C83S stimulated significantly lower cytokine secretion and did not appear to bind to TLR4 expressing cells. Thus it appears as though the results demonstrating that Prx1 interacts with TLR4 are not due to the presence of LPS contamination.

Prx1, HSP72 and HMGB1 not appear to have significant structural similarity nor do these molecules appear to share homology with LPS. Prx1, HSP72 and HMGB1 are molecular chaperones and the lack of structural homology between HSP72/HMGB1 and other TLR4 ligands has led some to speculate that the chaperone cargo rather than the chaperone is being recognized by TLR4. In support of this hypothesis, recent studies have shown that HMGB1 binding to TLR9 is a result of TLR9 recognition of HMGB1/DNA complexes. Extracellular Prx1 is present as a decamer, which is associated with Prx1 chaperone activity (Wood, et al. 2002. Biochemistry 41:5493-5504, the disclosure of which is incorporated herein by reference) and our studies indicate that Prx1 binding to TLR4 was dependent upon the ability to form decamers (FIGS. 3 and 4B). Thus it is possible that Prx1 binding of TLR4 is due to recognition of its cargo rather than of Prx1 itself. Nevertheless, agents that interfere with Prx1 binding to TLR4 according to the invention are expected to inhibit angiogenesis.

The Prx1C83S mutant, which lacks chaperone activity and exists primarily as a dimer (Wood, et al. 2002. Biochemistry 41:5493-5504) did not appear to bind to TLR4 (FIG. 4B); however the purified mutant protein was able to stimulate cytokine secretion from macrophages (FIG. 4A). Assays for biological function are traditionally more sensitive than binding assays and it is possible that the interaction of the dimeric form of Prx1 with TLR4 was below the level of detection in the binding assay employed in these studies. A small portion of Prx1C83S is present as a tetramer, which may also be able to interact with TLR4 at a level that is below detection, but that is sufficient to stimulate cytokine secretion.

Prx1 stimulation of cytokine secretion was dependent on TLR4 and MyD88 (FIGS. 3, 4 and 5); however, FITC-labeled Prx1 did bind to macrophages isolated from TLR4$^{-/-}$ (B10ScNJ) mice (FIG. 4B), albeit at a lower level than bound to macrophages isolated from TLR4$^{+/+}$ (B6) mice. Examination of the interaction of Prx1 with TLR4 at a cellular level indicated that while a majority of the TLR4 was internalized upon Prx1 binding, at least a portion of the Prx1 remained on the cell surface (FIG. 3B/C). These findings could be the result of excess Prx1 or alternatively that Prx1 is binding to additional receptors. Other TLR4 binding DAMPs have been shown to bind to multiple danger receptors and in some cases DAMP binding to TLR4 requires co-receptors. PbA, the malaria homolog of Prx1 requires MD2 to bind to TLR4; our studies indicate that Prx1 stimulation of cytokine secretion is optimal in the presence of serum and that antibodies to CD14 and MD2 block cytokine secretion from Prx1 stimulated cells. Furthermore, immunoprecipitated complexes of TLR4 and Prx1 contain MD2 and CD14, suggesting that these proteins contribute to the binding of Prx1 to TLR4.

EXAMPLE 3

We tested the efficacy of using Prx1 as an adjuvant for anti-tumor vaccines. Results are shown in FIG. 9 and demonstrate that Prx1 augments anti-tumor vaccine efficacy.

To obtain the data presented in FIG. 9, naïve mice were vaccinated with whole cell tumor lysate alone or in combination with 20 nM recombinant Prx1. After one week of rest, mice were challenged by injection of live tumor cells. Tumor growth was monitored for 60 days; n=10 mice/group. As shown in FIG. 9, Prx1 stimulates the efficacy of anti-tumor vaccines against Colon 26 tumors induced in the mice using Colon 26 murine colocarcinoma cells.

We claim:

1. A method for stimulating an immune response to an antigen in an individual comprising administering to the individual a pharmaceutical composition comprising the antigen and an isolated human Prx1 protein and a pharmaceutically acceptable carrier, wherein the isolated Prx1 protein is present in a Prx1 decamer.

2. The method of claim 1, wherein the antigen is a tumor antigen.

3. The method of claim 1, wherein the individual is diagnosed with or is suspected of having a cancer, wherein cells of the cancer express the antigen.

4. The method of claim 1, wherein the composition further comprises antigen presenting cells.

5. The method of claim 4, wherein the antigen presenting cells are dendritic cells, macrophages, or combinations thereof.

* * * * *